United States Patent
Li et al.

(10) Patent No.: US 10,470,720 B2
(45) Date of Patent: Nov. 12, 2019

(54) HEART RATE ACTIVITY DETECTING SYSTEM BASED ON DYNAMIC IMAGES AND METHOD THEREOF

(71) Applicant: Industrial Technology Research Institute, Hsinchu (TW)

(72) Inventors: Tsung-Hua Li, Hsinchu (TW); Rong-Rong Chen, Hsinchu (TW); Yi-Fei Luo, Hsinchu (TW); Ming-Chieh Tsai, Hsinchu (TW)

(73) Assignee: Industrial Technology Research Institute, Hsinchu, Taiwan (CN)

( * ) Notice: Subject to any disclaimer, the term of this patent is extended or adjusted under 35 U.S.C. 154(b) by 203 days.

(21) Appl. No.: 15/392,701

(22) Filed: Dec. 28, 2016

(65) Prior Publication Data
US 2018/0182095 A1    Jun. 28, 2018

(51) Int. Cl.
*A61B 5/00* (2006.01)
*H04N 5/235* (2006.01)
(Continued)

(52) U.S. Cl.
CPC ........ *A61B 5/7278* (2013.01); *A61B 5/02416* (2013.01); *H04N 1/6008* (2013.01); *H04N 5/2351* (2013.01)

(58) Field of Classification Search
CPC .. G09G 2360/144; G02F 2001/133618; H04N 5/58
See application file for complete search history.

(56) References Cited

U.S. PATENT DOCUMENTS 9,339,210 B2    5/2016    Kersten et al.
9,364,157 B2    6/2016    Lu et al.
(Continued)

FOREIGN PATENT DOCUMENTS

CN    101483763 A    7/2009
TW    M279846 U    11/2005
(Continued)

OTHER PUBLICATIONS

Haan, Gerard and Jeanne, Vincent, "Robust Pulse Rate from Chrominance-Based rPPG," IEEE Transactions on Biomedical Engineering, (2013), pp. 2878-2886.
(Continued)

*Primary Examiner* — Clifford Hilaire
(74) *Attorney, Agent, or Firm* — Mintz Levin Cohn Ferris Glovsky and Popeo, P.C.; Peter F. Corless; Steven M. Jensen

(57) ABSTRACT

Provided is a heart rate activity detecting method based on dynamic images. The method includes tracking a moving object. Preset brightness is determined based on an ambient condition. An image of the moving object is captured to generate a corresponding RGB color space, which is then converted to an image color space with adjustable brightness. The brightness of the image color space is adjusted according to the preset brightness to generate an image with corrected brightness, which is then converted to a RGB color space with the corrected brightness for calculating a heart rate activity of the moving object. The disclosure is capable of addressing the issue of an unstable light source by adjusting the brightness of the dynamic images, and then calculating the heart rate activity of the moving object according to the dynamic images. A heart rate activity detecting system based on dynamic images is also provided.

18 Claims, 6 Drawing Sheets
(1 of 6 Drawing Sheet(s) Filed in Color)

(51) Int. Cl.
*H04N 1/60* (2006.01)
*A61B 5/024* (2006.01)

(56) References Cited

U.S. PATENT DOCUMENTS

| | | | |
|---|---|---|---|
| 2006/0127081 A1* | 6/2006 | Lee | G09G 3/3406 396/282 |
| 2009/0219244 A1* | 9/2009 | Fletcher | G09G 3/3406 345/102 |
| 2011/0043864 A1* | 2/2011 | Tian | H04N 1/3878 358/3.26 |
| 2013/0310660 A1* | 11/2013 | Zuckerman-Stark | G16H 50/30 600/301 |
| 2016/0059078 A1 | 3/2016 | Liao | |
| 2016/0089041 A1* | 3/2016 | Keat | A61B 5/72 600/479 |
| 2018/0120661 A1* | 5/2018 | Kilgore | G02F 1/155 |

FOREIGN PATENT DOCUMENTS

| | | |
|---|---|---|
| TW | 201517870 A | 5/2015 |
| TW | I527611 B | 4/2016 |

OTHER PUBLICATIONS

Monkaresi, H. et al, "A machine Learning Approach to Improve Contactless Heart Rate Monitoring Using a Webcam," IEEE Journal of biomedical and health informatics, (2014) pp. 1153-1160.

* cited by examiner

US 10,470,720 B2

HEART RATE ACTIVITY DETECTING SYSTEM BASED ON DYNAMIC IMAGES AND METHOD THEREOF

TECHNICAL FIELD

The disclosure relates to heart rate detecting techniques, and relates to a hear rate activity detecting method based on dynamic images and a system thereof.

BACKGROUND

One of the common ways for detecting heart rates used by many existing sports equipment requires a user to hold onto metal heartbeat sensing grips provided on the sports equipment before heart rates can be measured. The shortcomings of this process include poor comfort, risk of electric shock, and hygiene concerns. Therefore, a non-contact detection method is suggested for determining heart rate activity, for example, through image recognition to determine the heart rate activity of a user.

However, there are many technical problems associated with capturing images and performing image recognition and processing while a user is using a sports equipment. In particular, when the user/subject is in motion, the camera on the sports equipment may also be in motion, e.g., shaking. In this circumstance, there is a relative movement between the camera and the subject, and an image thus captured is called a dynamic image, which is different from a static image in which there is no relative movement between the camera and the subject. Image processing for dynamic images is generally significantly more complex than the image processing for static images. For example, dynamic images will have problems such as image blurs, tracking of a region of interest (ROI), and light source correction. Image blurs are usually caused by shaking of the camera and/or the subject. When an ROI is selected and being tracked, light distributions of continuous frames of the ROI may vary due to the relative movements. For example, when a user is moving vigorously, if the facial area of the user is fixed, which is equivalent to a vigorously moving environment, there will be uneven ambient light distribution. This will result in errors in image analysis. Therefore, in order to use dynamic image analysis for determining heart rate activity of the user, the problem associated with light instability must be resolved.

If a heart rate activity detection based on dynamic images is performed using a heart rate activity detection technique based on static images, peak offsets may occur, which lead to calculation errors of the heart rates. If the heart rate detection technique based on static images is used and adjusted using a RGB color space, there will be two problems. The first problem is that, under a fixed light source, R, G, B coefficients for creating color channels of this ambient condition are constant. However, due to the relative motions between the camera and the subject, light conditions will not be the same, and, therefore, the heart rate detection technique based on static images cannot be applied to dynamic images. The second problem is that, if a RGB color space is used for image correction, the brightness and the saturation will also be changed. In this case, the saturation component of each of the original RGB color channels will also be changed, thereby affecting the reliability of using the RGB color space for heart rate detection.

SUMMARY

The disclosure provides a heart rate activity detecting method based on dynamic images, which may include: tracking a moving object; determining preset brightness based on an ambient condition; capturing an image of the moving object to generate a corresponding RGB color space, and converting the RGB color space to an image color space with adjustable brightness; adjusting the brightness of the image color space according to the preset brightness to generate an image with corrected brightness; and converting the image with the corrected brightness to a RGB color space with the corrected brightness for calculating a heart rate activity of the moving object.

The disclosure provides a heart rate activity detecting system based on dynamic images, which may include: an image sensing module configured for capturing images of a moving object; a processing module connected with the image sensing module and configured for determining preset brightness based on an image of the moving object and generating an image with corrected brightness based on the preset brightness; a heart rate activity detecting module connected with the processing module and configured for calculating a heart rate activity of the moving object based on the image with the corrected brightness; and a storage module connected with the image sensing module and the processing module and configured for storing the preset brightness and the images of the moving object.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
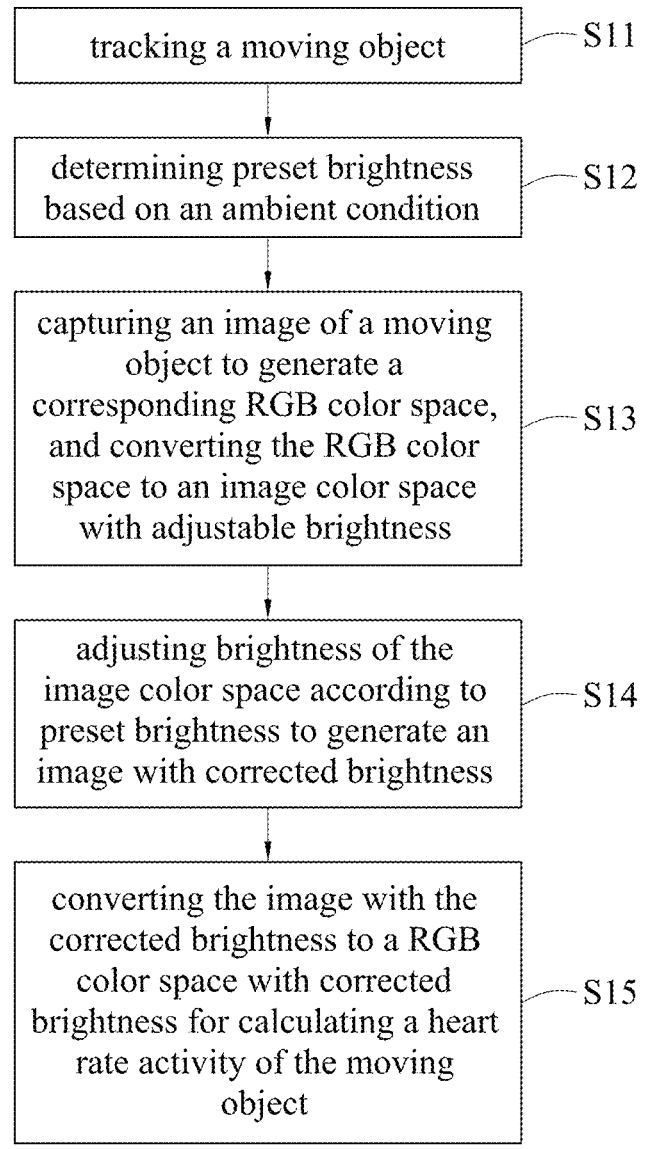
FIG. 1 is a flowchart illustrating a heart rate activity detecting method based on dynamic images in accordance with the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. Referring to FIG. 1, a heart rate activity detecting method based on dynamic images in accordance with the disclosure is shown. In an embodiment, the heart rate activity detecting method based on dynamic images in accordance with the disclosure addresses the issue of an unstable light source by adjusting the brightness of the dynamic images, such that the color space approximates the conditions of static images, and can thus be used for calculating the heart rate activity of a subject. Details of the method are below.

In step S11, a moving object is being tracked. A moving object, such as a user doing sports, is being tracked, and images of the moving object are continuously captured.

In step S12, preset brightness is determined based on an ambient condition. In order to adjust the brightness of dynamic images so as to minimize the factor attributed to an unstable light source, preset brightness is decided based on an ambient condition. The preset brightness is selected based on a threshold determined by peaks in the frequency domain of several images captured.

In an embodiment, the frequency domain peaks are determined based on frequency domain peaks of the green, red, or blue values of a plurality of images.

In another embodiment, the preset brightness can be determined from a RGB color space, and stored in a database for adjusting the brightness in a subsequent step. The database may also store the images.

In step S13, an image of the moving object is captured to generate a corresponding RGB color space, and the RGB color space is converted into an image color space with adjustable brightness. In step S13, a corresponding RGB color space is generated from the captured image, but brightness cannot be adjusted alone in the RGB space. In other words, the color value of R, G or B can be adjusted, but the brightness cannot be adjusted directly. Thus, step S13 converts the RGB color space into an image color space with adjustable brightness. In an embodiment, the image color space can be a YUV color space, a Lab color space or the like.

In step S14, the brightness of the image color space is adjusted according to the preset brightness to generate an image with corrected brightness. As described in step S13, after an image color space with adjustable brightness is generated, step S14 adjusts the brightness of the image color space according to the preset brightness, so as to generate an image with corrected brightness. In other words, after the brightness of the image is adjusted, errors in image recognition due to an unstable light source can be eliminated.

In step S14, a distribution function and the threshold determined based on peak values of a plurality of image previously captured can be used to determine if brightness should be corrected. That is, the threshold is used for determining if the brightness should be adjusted. In an embodiment, the distribution function is obtained from a binary search algorithm.

In step S15, the image with the corrected brightness is converted to a RGB color space with the corrected brightness. As such, the heart rate activity of the moving object can be calculated based on the R, G, and B color values in the RGB color space.

In step S15, an entropy is obtained from a slope between the peak and trough of the frequency domain peak in order to calculate the heart rate activity of the moving object.

In step S11, tracking a moving object refers to tracking a region of interest (ROI). In an embodiment, calculations associated with ROI tracking can be provided by OpenCV library.

In step S11, tracking a moving object also includes image blur processing. In an embodiment, the image blur processing can be carried out by exposure solutions processing, inertial sensors and Point Spread Function (PSF), or a frequency-domain iterative updates approach.

Figure 2A:
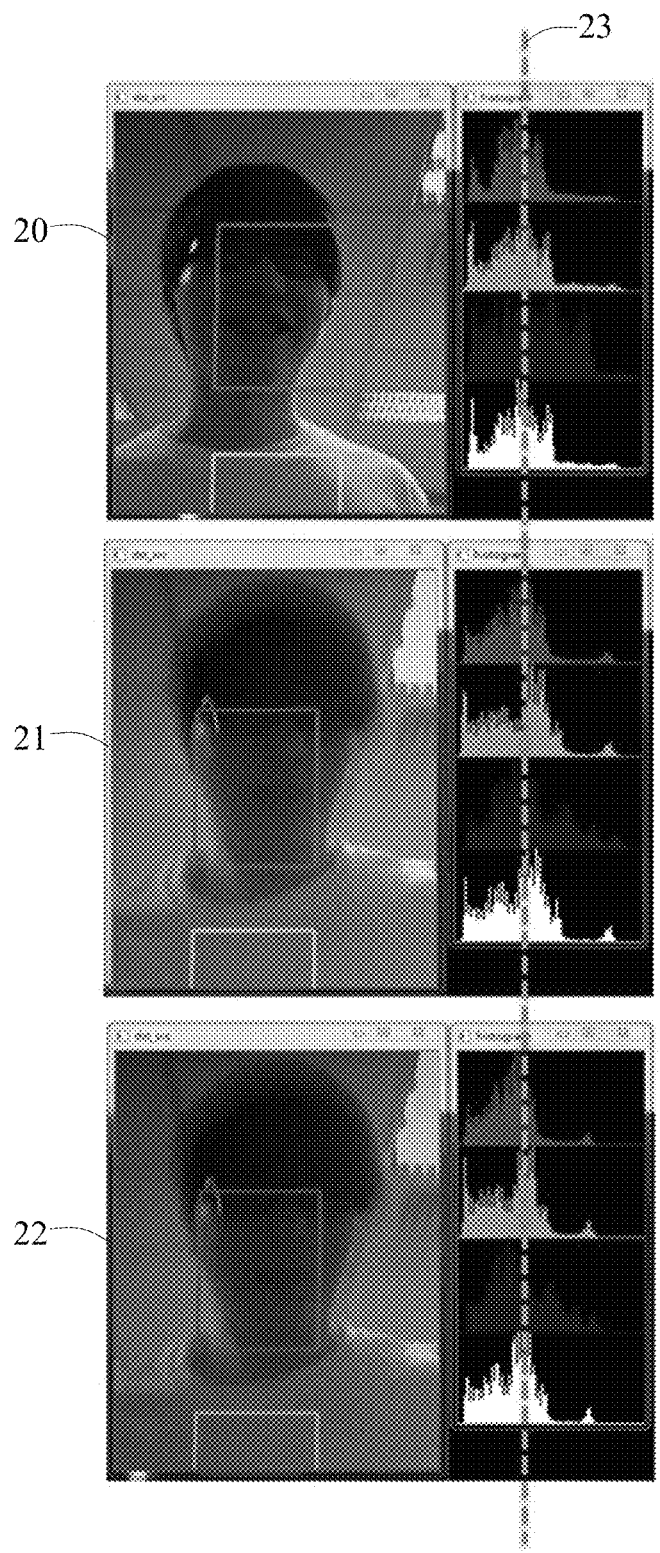
FIGS. 2A and 2B are diagrams illustrating the determination of preset brightness and the adjustment of brightness for a dynamic image in accordance with the disclosure.

Referring to FIG. 2A, a diagram illustrating the determining of the preset brightness and the adjustment of brightness for a dynamic image in accordance with the disclosure is shown. A picture 20 represents a static image with 100% of brightness. A picture 21 represents a dynamic image with 100% of brightness. The image of the picture 21 can be converted into a YUV color space in order to adjust the brightness (Y) to create a dynamic image with 85% of brightness shown by a picture 22. Other brightness values can be used, for example, 130%. A dashed line 23 represents a threshold determined from the image (the picture 20) with the preset brightness.

After the brightness is adjusted, the difference between the peak of each color in the converted RGB color space and the threshold is determined, and an image with the smallest difference, 85% of brightness in an embodiment, is selected as the image with the corrected brightness. The image with the corrected brightness is converted to a RGB color space with the corrected brightness for subsequent calculation of the heart rate activity.

The disclosure proposes a solution that addresses the interference during dynamic image analysis of heart rate activity caused by a variable light source, and an image pre-processing for image analysis of heart rate activity is performed. The influence on the saturation is reduced during adjustment of the brightness. Therefore, before R, G, B is used for heart rate activity analysis, another color space is used for adjusting the brightness alone, after the brightness is adjusted, and the image color space is converted to a RGB color space for heart rate activity analysis using R, G and B values. In an embodiment, a YUV color space is used for adjusting the Y component (brightness), which is then converted to a RGB color space. By now, the adjustment in Y is reflected on adjustments in R, G, and B values.

According to the above principle, a reference image with preset brightness can be determined, a dynamic image is then captured for color space calculation, and an image with corrected brightness is thus generated. Finally, heart rate activity is calculated based on a plurality of the continuous images.

The conversion of a RGB color space to a YUV color space is illustrated in the following example. In general, Y'UV signals are generated by RGB signals. R, G, and B have different weights, for example, $W_R=0.299$, $W_G=0.114$, and $W_B=1-W_R-W_B=0.587$. Assuming $U_{max}=0.436$ and $V_{max}=0.615$, Y'UV can be obtained from RGB through the following formulae:

$$Y' = W_R R + W_G G + W_B B = 0.299R + 0.587G + 0.114B$$

$$U = U_{max} \frac{B - Y'}{1 - W_B} \approx 0.492(B - Y')$$

$$V = V_{max} \frac{R - Y'}{1 - W_R} \approx 0.544(R - Y')$$

$$Y', U, \text{ and } V \text{ are } [0, 1] \backslash [-U_{max}, U_{max}] \backslash [-V_{max}, V_{max}]$$

$$R = Y' + V \frac{1 - W'_R}{V_{max}} = Y' + \frac{V}{0.877} = Y' + 1.14V$$

$$G = Y' - U \frac{W_B(1 - W_B)}{U_{max} W_G} - V \frac{W_R(1 - WR)}{V_{max} W_G} =$$

$$Y' - \frac{0.232U}{0.587} - \frac{0.341V}{0.587} = Y' - 0.395U - 0.571V$$

$$B = Y' + U \frac{1 - W_B}{U_{max}} = Y' + \frac{U}{0.492} = Y' + 2.033U$$

-continued $$\begin{bmatrix} Y' \\ U \\ V \end{bmatrix} = \begin{bmatrix} 0.299 & 0.587 & 0.114 \\ -0.14713 & -0.28886 & 0.436 \\ 0.615 & -0.51499 & -0.10001 \end{bmatrix} \begin{bmatrix} R \\ G \\ B \end{bmatrix}$$

$$\begin{bmatrix} R \\ G \\ B \end{bmatrix} = \begin{bmatrix} 1 & 0 & 1.13983 \\ 1 & -0.39465 & -0.58060 \\ 1 & 2.03211 & 0 \end{bmatrix} \begin{bmatrix} Y' \\ U \\ V \end{bmatrix}$$

In addition, an iteration equation is used for image de-blurring. The iteration function is given below:

```
int fac(int n)
{if (n≤1) return 1;
    else return n*fac(n−1)
}
int fib(int n)
{if (n≤1) return 1;
    else return fib(n−1)*fib(n−2)
}
```

Figure 2B:
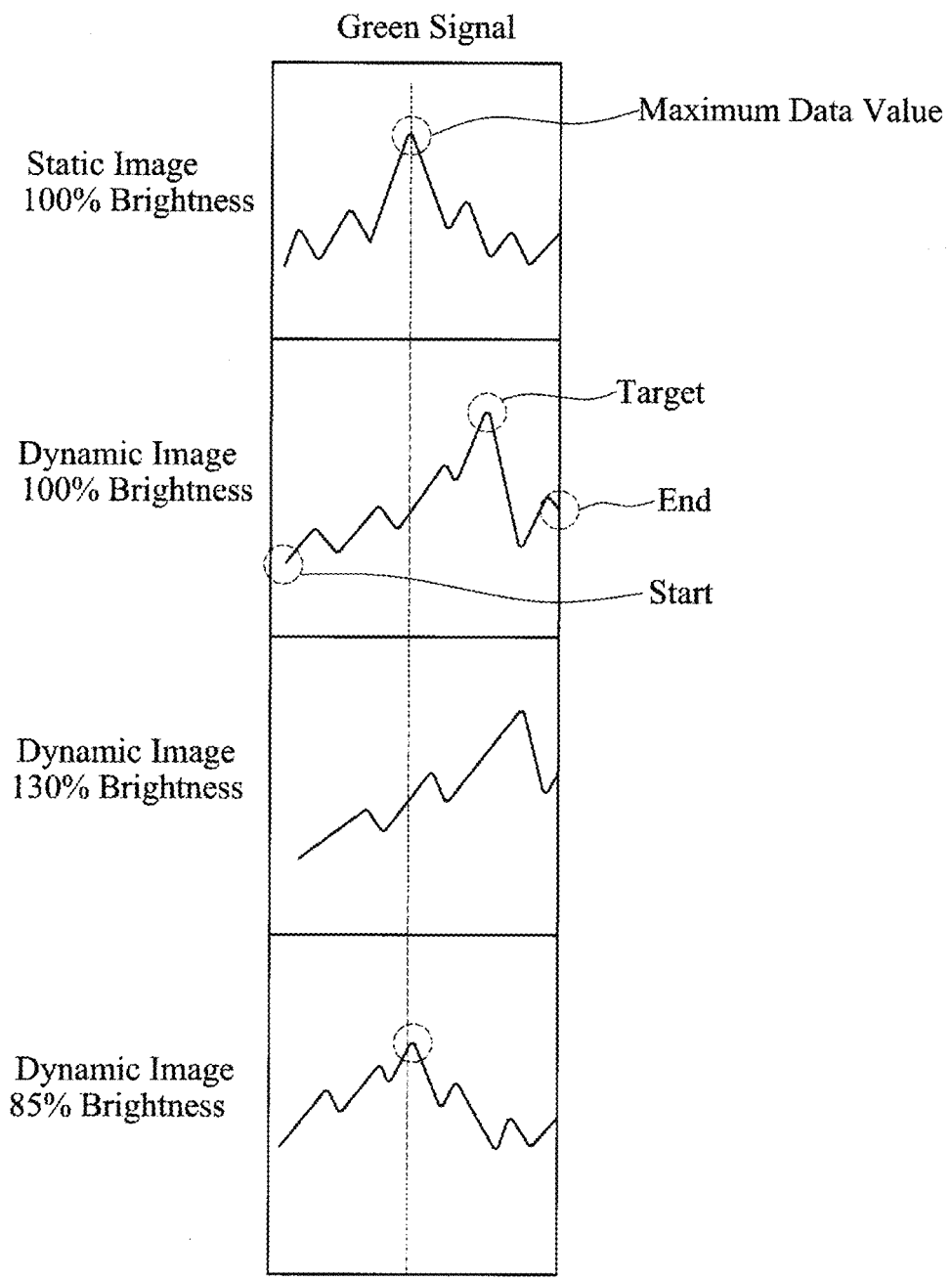

Moreover, a binary search algorithm can be used to obtain a dynamic image with corrected brightness that approximates the conditions of the static image. As shown in FIG. 2B, with regard to the green signal in RGB colors, in a static image with 100% of brightness (the top block), the maximum data value is the threshold determined by the frequency domain peak, and is denoted by data [center]. The leftmost side of the signal is the start, and the rightmost side thereof is the end.

The brightness of a dynamic image is adjusted to 100% (no adjustment), 130%, and 85%, shown by the three blocks underneath the top one, respectively. Examining the image with 100% of brightness, since its target is greater than data[center], an equation (target+start)/2 is used to move target towards data[center]. On the contrary, if target is smaller than data[center], an equation (target+end)/2 is used to move target towards data[center].

When target is close to data[center], as shown by the dynamic image with 85% of brightness, the colors of an image after brightness adjustment will approximate the conditions of the static image. Therefore, this dynamic image with the corrected brightness can be used for heart rate activity analysis.

Figure 3:
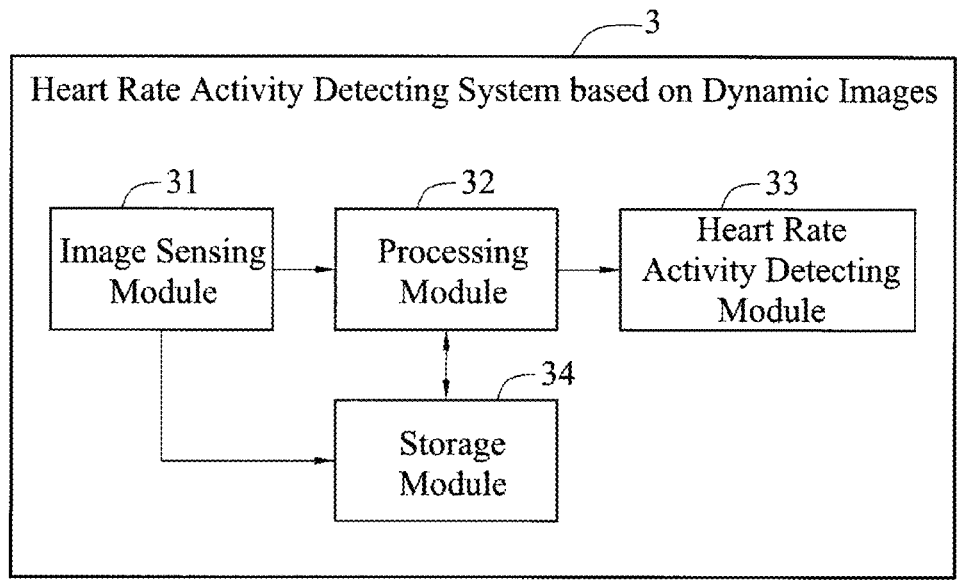
FIG. 3 is a schematic diagram depicting a heart rate activity detecting system based on dynamic images in accordance with the disclosure.

Referring to FIG. 3, a schematic diagram depicting a heart rate activity detecting system 3 based on dynamic images in accordance with the disclosure is shown. The heart rate activity detecting system 3 includes an image sensing module 31, a processing module 32, a heart rate activity detecting module 33 and a storage module 34.

The image sensing module 31 is configured for capturing an image of a moving object. The image sensing module 31 can be a device with a video or photographic function. For example, the image sensing module 31 can be a camera or an image capturing device.

The processing module 32 is connected with the image sensing module 31 and configured for determining preset brightness based on the image, and generating an image with corrected brightness based on the preset brightness. In an embodiment, the processing module 32 is the calculation core for the heart rate activity detecting system 3 based on dynamic images and is configured for determining preset brightness based on the captured image, and generating an image with corrected brightness based on the preset brightness.

The heart rate activity detecting module 33 is connected with the processing module 32 and is configured for obtaining the heart rate activity of the moving object based on the image with the corrected brightness. The heart rate activity detecting module 33 is used for obtaining the heart rate activity, that is, performing operations using R, G and B color values. The processing module 32 and the heart rate activity detecting module 33 can be implemented as a processor for generating the image with corrected brightness and obtaining the heart rate activity.

The storage module 34 is connected with the image sensing module 31 and the processing module 32 for storing the preset brightness and the images described before. For example, the storage module 34 can be a storage.

Figure 6:
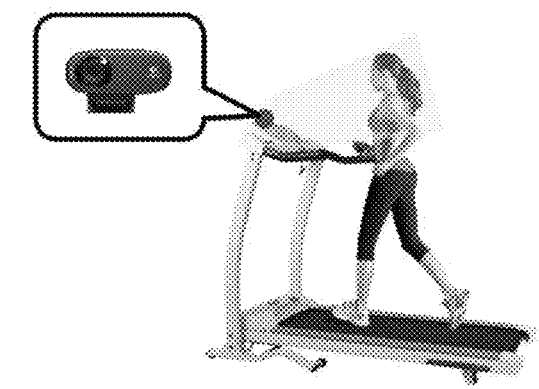
FIG. 6 is a schematic diagram illustrating the heart rate activity detecting system based on dynamic images under different applications in accordance with the disclosure.
Figure 6:
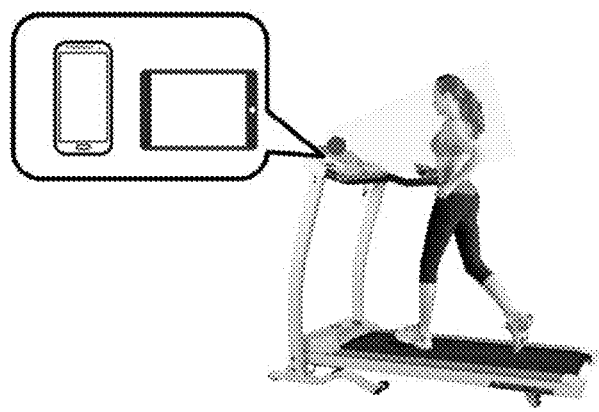

In an embodiment, the image sensing module 31 can be combined with a sports equipment or a portable electronic device. In an embodiment, the portable electronic device is a mobile device, a tablet, a laptop, a mobile phone or a camera. Therefore, in one implementation, as shown in FIG. 6, the image sensing module 31 can be fixed or embedded in the sports equipment, or integrated with a mobile phone or tablet. During exercising, the mobile phone or tablet is placed flat on the sports equipment for capturing images of a user.

Figure 4:
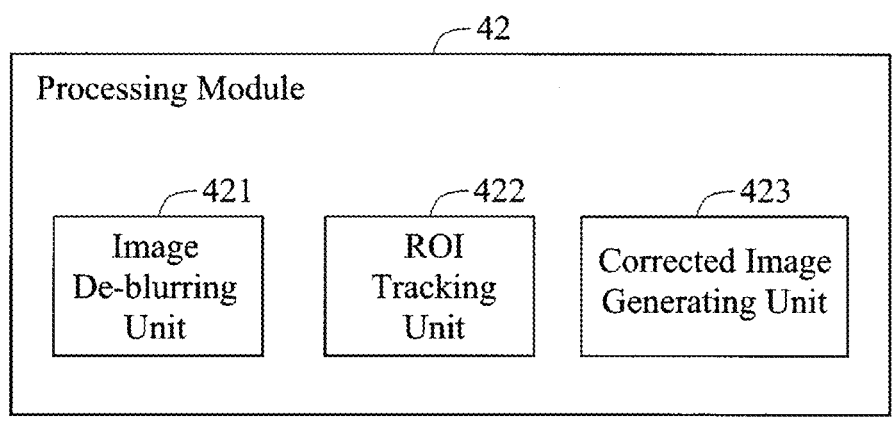
FIG. 4 is a schematic diagram depicting various units for dynamic image processing in a processing module in accordance with the disclosure.

Referring to FIG. 4, a schematic diagram depicting various units for dynamic image processing in the processing module in accordance with the disclosure is shown. As described previously, a processing module 42 is the calculation core of the heart rate activity detecting system based on dynamic images, and further includes an image de-blurring unit 421, a ROI tracking unit 422 and a corrected image generating unit 423 for processing of dynamic images.

The image de-blurring unit 421 is configured for getting rid of blurs in the images. The image de-blurring unit 421 may perform a de-blurring composite analysis procedure, that is, de-blurring composite computational analysis, on each color image to obtain color images with no blurs. The de-blurring composite analysis procedure may include image restoration, filtering, and iteration methods.

The ROI tracking unit 422 tracks a region of interest (ROI) of the moving object through OpenCV library. The ROI tracking unit 422 primarily locks onto the ROI of the moving object and performs tracking thereof. In an embodiment, the ROI constantly stays at the center of the image.

The corrected image generating unit 423 determines if brightness correction is needed using a distribution function and the preset brightness. The corrected image generating unit 423 is used for determining if brightness correction is required. The determination process is as described previously. An image is converted into a RGB color space, the difference between the peak and the threshold of each color in the RGB color space is calculated, and the image with the smallest difference is selected as the image with the corrected brightness. In an embodiment, the peak of each color in the RGB color space is obtained from the maximum value in a corresponding color distribution histogram of the RGB color space of the dynamic image, while the threshold is obtained from the maximum value in a corresponding color distribution histogram of the RGB color space of a static image. In an embodiment, calculating the difference between the peak and the threshold means comparing the maximum values of the dynamic image and the static image.

Figure 5:
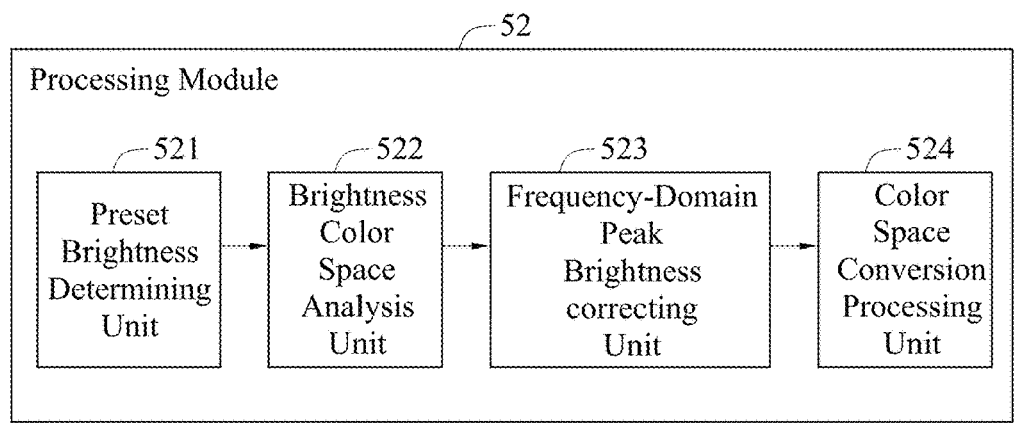
FIG. 5 is a schematic diagram depicting various units for adjusting brightness in the processing module in accordance with the disclosure.

Referring to FIG. 5, a schematic diagram depicting various units for adjusting brightness in the processing module in accordance with the disclosure is shown. As mentioned previously, the processing module 52 is the calculation core of the heart rate activity detecting system based on dynamic images, such that the processing module 52 further includes a preset brightness determining unit 521, a brightness color space analysis unit 522, a frequency-domain peak brightness correcting unit 523 and a color space conversion processing unit 524 for brightness processing of the dynamic image.

The preset brightness determining unit 521 is configured for determining preset brightness based on an ambient condition. In order to adjust the brightness of a dynamic image so as to minimize the effect of an unstable light source, preset brightness is first determined based on the ambient condition. In an embodiment, the preset brightness can be determined by frequency-domain peaks and a threshold. The frequency-domain peaks are determined from the frequency-domain peaks of the green, red or blue values of a plurality of images captured, and the threshold is determined by these frequency-domain peaks.

The brightness color space analysis unit 522 is configured for converting the preset brightness into RGB colors. The brightness color space analysis unit 522 converts the preset brightness into RGB colors for subsequent comparison between the preset brightness image and the dynamic image.

The frequency-domain peak brightness correcting unit 523 converts RGB colors into YUV colors. The YUV colors can be used for brightness adjustment. As described previously, the YUV color space allows adjustment of brightness alone, so the frequency-domain peak brightness correcting unit 523 converts the RGB colors into YUV colors and adjusts the brightness of the dynamic image based on the preset brightness.

In an embodiment, the brightness of the preset static image of the moving object may be greater than the brightness of the dynamic image of the moving object. Alternatively, the brightness of the dynamic image of the moving object may be greater than the brightness of the preset static image of the moving object. Therefore, the frequency-domain peak brightness correcting unit 523 can adjust the brightness of the dynamic image according to these two situations, in order for the brightness of the dynamic image to approximate or equals to the brightness of the static image.

The color space conversion processing unit 524 converts YUV colors into corrected RGB colors. After the preset brightness is determined and the brightness of the dynamic image is adjusted based on the preset brightness, for subsequent calculation of heart rate activity, the YUV colors are converted into corrected RGB colors. The R, G and B in this corrected RGB colors allow for the calculation of heart rate activity.

The previous descriptions illustrate an image pre-processing before image analysis of heart rate activity, that is, adjustment of brightness of a dynamic image so that its color space approximates that of a static image. As such, after brightness adjustment, the heart rate activity can be calculated using heart rate activity detecting technique that is based on static images. The applicant has already proposed a heart rate activity detecting technique based on static images in TW Patent No. 102141509, and the disclosure describes the image pre-processing of a dynamic image before such a heart rate activity detecting technique based on static images can be used. The image processing related to static images is not described in details hereinafter.

Figure 7:
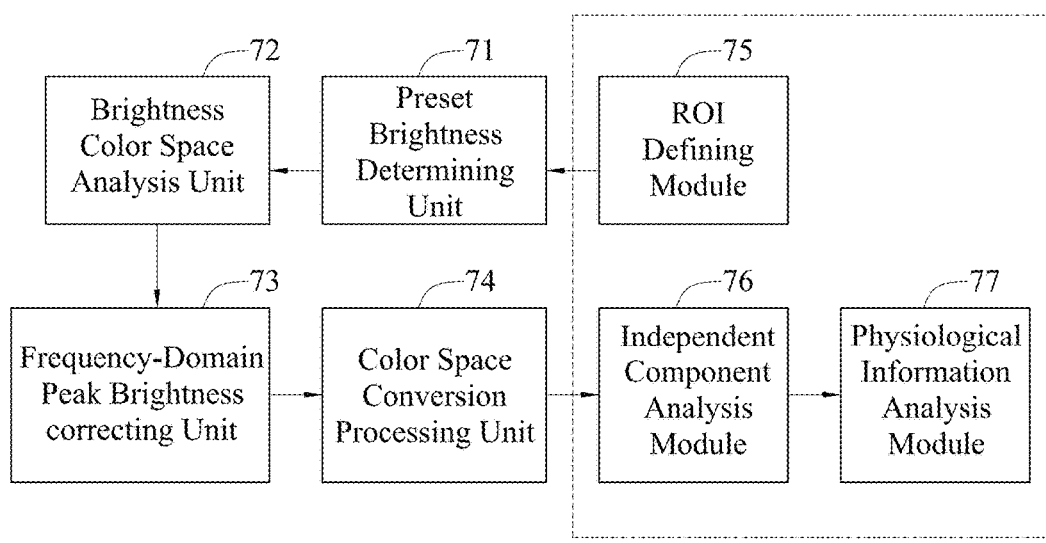
FIG. 7 is a schematic diagram depicting a heart rate activity detecting process based on dynamic images combined with static images in accordance with the disclosure.

Referring to FIG. 7, a schematic diagram depicting a heart rate activity detecting process combining dynamic images and static images in accordance with the disclosure is shown. A preset brightness determining unit 71, a brightness color space analysis unit 72, a frequency-domain peak brightness correcting unit 73 and a color space conversion processing unit 74 are the same as the preset brightness determining unit 521, brightness color space analysis unit 522, frequency-domain peak brightness correcting unit 523 and color space conversion processing unit 524 described with respect to FIG. 5, respectively, and thus will not be described.

In an embodiment, the heart rate activity detecting system based on dynamic images further includes a ROI defining module 75 connected with the preset brightness determining unit 71. The ROI defining module 75 is configured for obtaining a ROI from the moving object. The ROI defining module 75 is able to define the ROI of the moving object in each color image by computational analysis of each color image based on preset skin color target conditions.

In an embodiment, the heart rate activity detecting system based on dynamic images further includes an independent component analysis module 76 connected with the color space conversion processing unit 74. The independent component analysis module 76 is configured for performing operations on the red channel signal, the green channel signal and the blue channel signal of the ROI to obtain a first independent component signal, a second independent component signal, and a third independent component signal. A frequency domain conversion process, a signal energy calculation process and a signal adaptation process are performed on the first independent component signal, the second independent component signal, and the third independent component signal of each ROI, thereby obtaining a filter signal.

In an embodiment, the heart rate activity detecting system based on dynamic images further includes a physiological information analysis module 77 connected with the independent component analysis module 76 for performing physiological information analysis, that is, performing physiological information analysis on filter signals in the facial area to obtain the heart rate activity of the moving object. The ROI defining module 75, the independent component analysis module 76 and the physiological information analysis module 77 can be implemented as a processor for defining the ROI of the moving object, performing conversion, calculation and adaptation processes, and performing physiological information analysis.

The heart rate activity detecting method based on dynamic images and system thereof in accordance with the disclosure determines a preset brightness, converts a captured image from a RGB color space to an image color space with adjustable brightness, adjusts the brightness of the image based on the preset brightness, and converts the image with the corrected brightness back to a RGB color space for calculating the heart rate activity of a user. In an embodiment, by converting a RGB color space to an image color space with an adjustable brightness, the problem associated with an unstable light source can be eliminated. In other words, by adjusting the brightness, the color space approximates the conditions in the static image, so that after brightness is adjusted, a procedure similar to an image processing technique based on static images can be used for calculating the heart rate activity.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A heart rate activity detecting method based on dynamic images, comprising:
tracking a moving object;
determining preset brightness based on an ambient condition in which the moving object is located, wherein the preset brightness is selected based on a threshold determined based on frequency-domain peaks of a plurality of images captured;
capturing an image of the moving object to generate a corresponding RGB color space, and converting the RGB color space to an image color space with adjustable brightness;
adjusting the brightness of the image color space according to the preset brightness to generate an image with corrected brightness, wherein adjusting the brightness of the image color space according to the preset brightness includes determining whether brightness is to be adjusted based on a distribution function and the threshold, wherein the distribution function is obtained through a binary search algorithm; and
converting the image with the corrected brightness to a RGB color space with the corrected brightness for calculating a heart rate activity of the moving object.

2. The heart rate activity detecting method of claim 1, wherein the frequency-domain peaks are determined from frequency-domain peaks of green, red or blue values of the plurality of images.

3. The heart rate activity detecting method of claim 1, wherein calculating the heart rate activity of the moving object includes obtaining an entropy based on slopes between a peak and a trough of the frequency-domain peaks.

4. The heart rate activity detecting method of claim 1, wherein the image color space is a YUV color space or a Lab color space.

5. The heart rate activity detecting method of claim 1, wherein the preset brightness is determined by a RGB color space.

6. The heart rate activity detecting method of claim 1, wherein tracking the moving object includes tracking a region of interest (ROI).

7. The heart rate activity detecting method of claim 1, wherein tracking the moving object includes an image de-blurring process carried out by exposure solutions processing, inertial sensors and Point Spread Function (PSF), or a frequency domain iterative updates approach.

8. A heart rate activity detecting system based on dynamic images, comprising:
an image sensing module configured for capturing images of a moving object;
a processing module connected with the image sensing module and configured for determining preset brightness based on an image of the moving object and generating an image with corrected brightness based on the preset brightness, the preset brightness being determined based on an ambient condition in which the moving object is located, wherein the preset brightness is selected based on a threshold determined based on frequency-domain peaks of a plurality of images captured, the processing module configured to determine whether brightness is to be adjusted based on a distribution function and the threshold, wherein the distribution function is obtained through a binary search algorithm;
a heart rate activity detecting module connected with the processing module and configured for calculating a heart rate activity of the moving object based on the image with the corrected brightness; and
a storage module connected with the image sensing module and the processing module and configured for storing the preset brightness and the images of the moving object.

9. The heart rate activity detecting system of claim 8, wherein the image sensing module is combined with a sports equipment.

10. The heart rate activity detecting system of claim 8, wherein the image sensing module is combined with a portable electronic device.

11. The heart rate activity detecting system of claim 10, wherein the portable electronic device is a mobile device, a tablet, a laptop, a mobile phone or a camera.

12. The heart rate activity detecting system of claim 8, wherein the processing module further includes:
an image de-blurring unit configured for eliminating blurs in the images;
a region of interest (ROI) tracking unit configured for tracking an ROI through OpenCV library; and
a corrected image generating unit configured for determining whether brightness is to be adjusted based on a Point Source Function and the preset brightness.

13. The heart rate activity detecting system of claim 8, wherein the processing module further includes:
a preset brightness determining unit configured for determining the preset brightness based on the ambient condition;
a brightness color space analysis unit configured for converting the preset brightness into RGB colors;
a frequency-domain peak brightness correcting unit configured for converting the RGB colors into YUV colors for adjusting brightness; and
a color space conversion processing unit configured for converting the YUV colors into RGB colors with corrected RGB colors.

14. The heart rate activity detecting system of claim 13, wherein when the brightness of a preset static image of the moving object is greater than the brightness of a dynamic image of the moving object, the frequency-domain peak brightness correcting unit adjusts the brightness of the dynamic image such that it approximates or equal to the brightness of the static image.

15. The heart rate activity detecting system of claim 13, wherein when the brightness of a dynamic image of the moving object is greater than the brightness of a preset static image of the moving object, the frequency-domain peak brightness correcting unit adjusts the brightness of the dynamic image such that it approximates or equal to the brightness of the static image.

16. The heart rate activity detecting system of claim 13, further comprising a region of interest (ROI) defining module connected with the preset brightness determining module and configured for obtaining a ROI from the moving object.

17. The heart rate activity detecting system of claim 16, further comprising an independent component analysis module connected with the color space conversion processing unit and configured for performing operations on a red channel signal, a green channel signal, and a blue channel signal of the ROI.

18. The heart rate activity detecting system of claim 17, further comprising a physiological information analysis module connected with the independent component analysis module and configured for performing physiological information analysis.

* * * * *